United States Patent
Heringa et al.

(10) Patent No.: US 6,730,216 B2
(45) Date of Patent: May 4, 2004

(54) CARRIER FOR A CHROMATOGRAPHIC COLUMN

(75) Inventors: Menno Heringa, Middelburg (NL); Jacobus Duvekot, Vrouwenpolder (NL)

(73) Assignee: Varian, B.V., Middelburg (NL)

( * ) Notice: Subject to any disclaimer, the term of this patent is extended or adjusted under 35 U.S.C. 154(b) by 0 days.

(21) Appl. No.: 09/978,110

(22) Filed: Oct. 15, 2001

(65) Prior Publication Data

US 2002/0100719 A1 Aug. 1, 2002

(30) Foreign Application Priority Data

Oct. 13, 2000 (NL) .............................................. 1016403

(51) Int. Cl.⁷ .............................................. B01D 15/08
(52) U.S. Cl. ...................... 210/198.2; 210/656; 422/83; 96/101
(58) Field of Search .............................. 210/656, 198.2, 210/175, 198.3, 635; 422/70, 83; 73/23.35, 23.42, 23.39; 95/82–88; 96/101–107; 284/175

(56) References Cited

U.S. PATENT DOCUMENTS

| | | | |
|---|---|---|---|
| 4,469,660 A | 9/1984 | Jones et al. | |
| 4,599,169 A | * 7/1986 | Ray | ........................... 210/175 |
| 5,005,399 A | 4/1991 | Holtzclaw et al. | |
| 5,808,178 A | 9/1998 | Rounbehler et al. | |
| 6,454,939 B1 | * 9/2002 | Haas et al. | .............. 210/198.3 |

FOREIGN PATENT DOCUMENTS

| | | |
|---|---|---|
| DE | G 86 26 875.9 U1 | 2/1987 |
| DE | 43 01 401 A1 | 7/1994 |
| JP | 07035737 | 2/1995 |

* cited by examiner

Primary Examiner—W. L. Walker
Assistant Examiner—K S Menon
(74) Attorney, Agent, or Firm—Bella Fishman

(57) ABSTRACT

An assembly consisting of a winding structure 1 around which a chromatographic column 6 can be wound, and an information carrier 7 which can be connected to said winding structure 1. This assembly offers a rigid and convenient means to handle one or two chromatographic columns of longer lengths. The information carrier 7 contains the chromatographic column identification information as well as several tools, such as a tool 13 to hold one or two chromatographic column connectors 11, a ruler to measure column insertion lengths and clips 12 to hold column ends, and clips to hold column extensions.

24 Claims, 3 Drawing Sheets

CARRIER FOR A CHROMATOGRAPHIC COLUMN

FIELD OF THE INVENTION

The present invention relates to a carrier for a chromatographic column assembly, and more particularly relates to a carrier in combination with a chromatographic column assembly.

BACKGROUND OF THE INVENTION

A chromatographic column assembly is a well known device, and comprises a winding structure or reel around which a chromatographic column is wound. This allows a long column to be accommodated. Such chromatographic columns can be used in several environments. For example, they are used in ovens where gasses are lead through the columns to achieve separation of sample components in an injected gas stream.

When several columns are placed in an oven, it is important to be able to identify each of the columns. There are several known information carriers for chromatographic columns, which identify columns. However, these known information carriers suffer from various disadvantages. Many known information carriers are attached to the column with a simple wire or thread (made of iron) which is not durable and, if they become detached, this often leads to misidentification of the column. Such simple wires or threads are typically formed of straightened conventional paper clips.

Also, when it is desired to connect two columns together, a large and heavy connector is used, which often causes damage in the area of the connection, which results in gas leakage in the region of the connection.

SUMMARY OF THE INVENTION

An object of the present invention is to allow the proper connection together of one or more winding structures and a carrier, which does not suffer from the disadvantages of the prior art described above.

According to a first aspect of the present invention, there is provided a carrier for a chromatographic column assembly, including at least one connecting part for connecting the carrier to the chromatographic column assembly.

The carrier may be an information carrier, including at least one part for displaying information, for example, to identify the column to a user. The carrier may be connected across opposite edges of an upper part of the winding structure of the column assembly. This may allow the carrier to be used as a toolbar or grip to handle the column assembly. The information carrier could take many different forms. For example, it could be in the form of a thread or wire on which identification means for the column are attached. The preferred design is, however, a strip form. That is, an elongate, generally planar sheet of material. Information can be recorded on the carrier by any known means, such as text, barcode, integrated circuit etc. It is a simple matter to put this information onto the carrier. The carrier may be manufactured separately or together with the column assembly. It is possible to have different materials for the column assembly and the information carrier. It is also possible to incorporate useful tools into or onto the carrier, such as a ruler with a centimeter or inch scale. This facilitates measurement of the insertion length of the column into an injector or detector of an oven.

One or more connectors may be attached to the carrier, the connectors being for coupling together different columns. The connectors allow a stable connection between two or more columns to be made, which is less likely to damage the columns than conventional connection methods.

The carrier may include means for accommodating two column assemblies of different diameter, one positioned within the other.

The carrier may be designed to provide a proper installation of the complete assembly in an oven. For example, it is possible to enlarge the carrier at one or both ends to accommodate connecting points to a member in an oven. Other connections in the oven are also possible with screws, etc. It is possible to connect further tools. For example, tools for accommodating column extensions.

The connection between the carrier and the winding structure of the column assembly can be made by any known connecting means. For example, where the winding structure is formed of wire, bent ends of the wire can be attached to the information carrier.

The carrier may be made from a material capable of bearing information, such as aluminum. Such a material can withstand high temperatures experienced in ovens. The design will be varied according to the application in question.

BRIEF DESCRIPTION OF THE INVENTION

For a better understanding of the present invention, an embodiment will now be described by way of example, with reference to the accompanying drawings, in which.

DETAILED DESCRIPTION OF THE INVENTION

Figure 1:
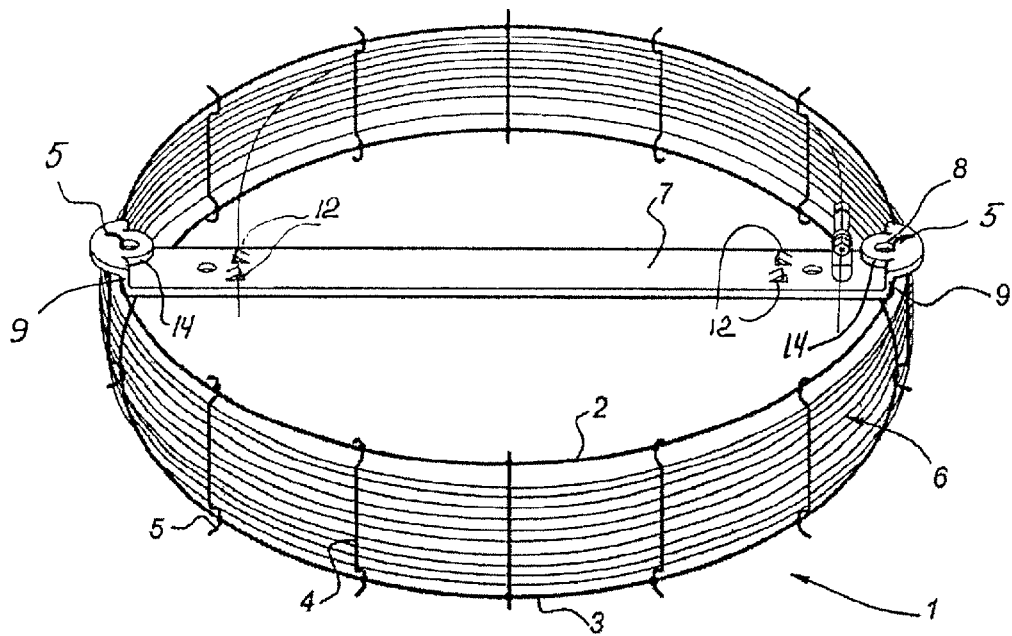
FIG. 1 shows a perspective view of a chromatographic column assembly with an information carrier attached thereto.

In FIG. 1, a chromatographic column assembly is shown generally at 1. The column assembly 1 includes a winding structure comprising an upper ring 2 of wire and a lower ring (or band) 3. The upper ring 2 and lower ring 3 are connected together by a plurality of wires 4 spaced apart generally equally around the circumference of each of the rings 2, 3. The connecting wires 4 are connected to the upper 2 and lower 3 rings by welding or any other suitable means. The connecting wires 4 include a substantially linear main portion, terminating at each end in a generally semicircular or hook-like portion 5. The connecting wires 4 are connected to the upper ring 2 and lower ring 3 at the convex portion of the semicircular or hook-like portion 5. The chromatographic column 6 is wound around the connecting wires 4, allowing a considerable length of chromatographic column to be stored in a relatively small volume.

A carrier 7 is mounted on the winding structure 1. The preferred material for the carrier 7 is metal, and preferably aluminum. The carrier 7 comprises a planar main body portion, with a step formed at each end thereof in the region where the carrier 7 lies adjacent to the upper ring 2. The upper surface of each stepped portion 9 has a tab 14 extending therefrom, cut from the carrier 7. These protruding tabs 14 can be used to hold column extensions. These extensions could be a bundle of windings of column from 1 to 15 meters in length. The stepped portions 9 each have an aperture 8 formed therein. These apertures are designed in such a way that the semicircular portion 5 of a connecting wire 4 can be accommodated therein, as shown particularly in enlarged FIG. 3. The semicircular portion 5 of the connection wires 4 at opposite sides of the winding structure 1 serve to clamp the carrier 7 to the upper ring 2 by the action of the semicircular portion 5 passing through the apertures 8.

Figure 2:
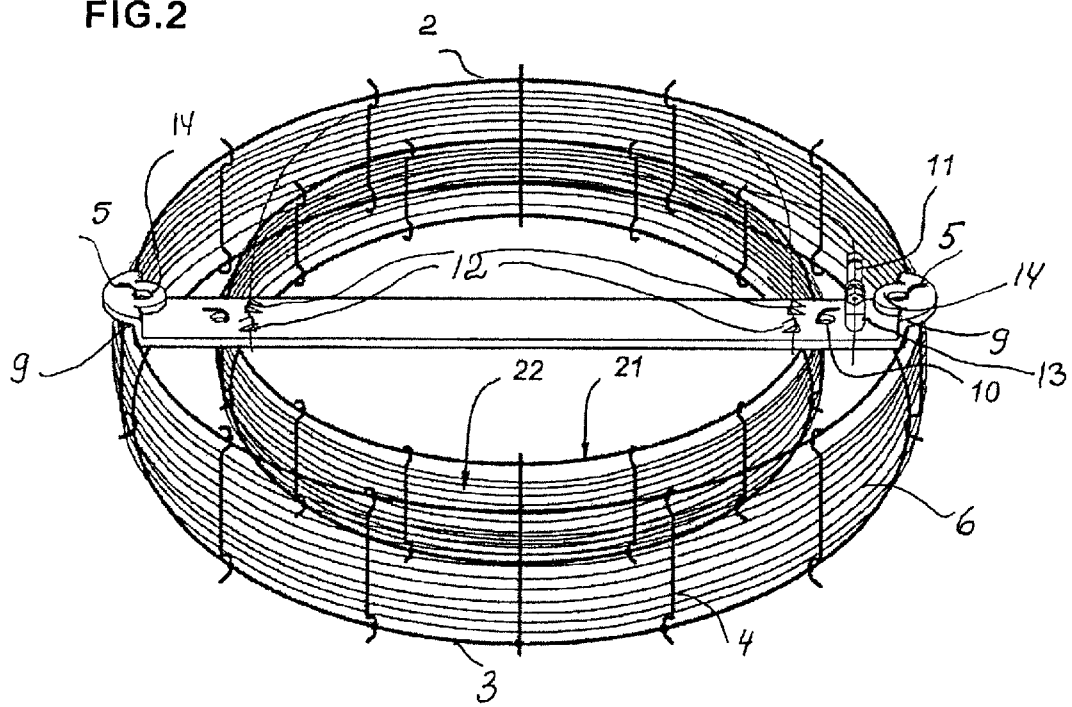
FIG. 2 shows a perspective view of two chromatographic column assemblies attached to an information carrier.
Figure 3:
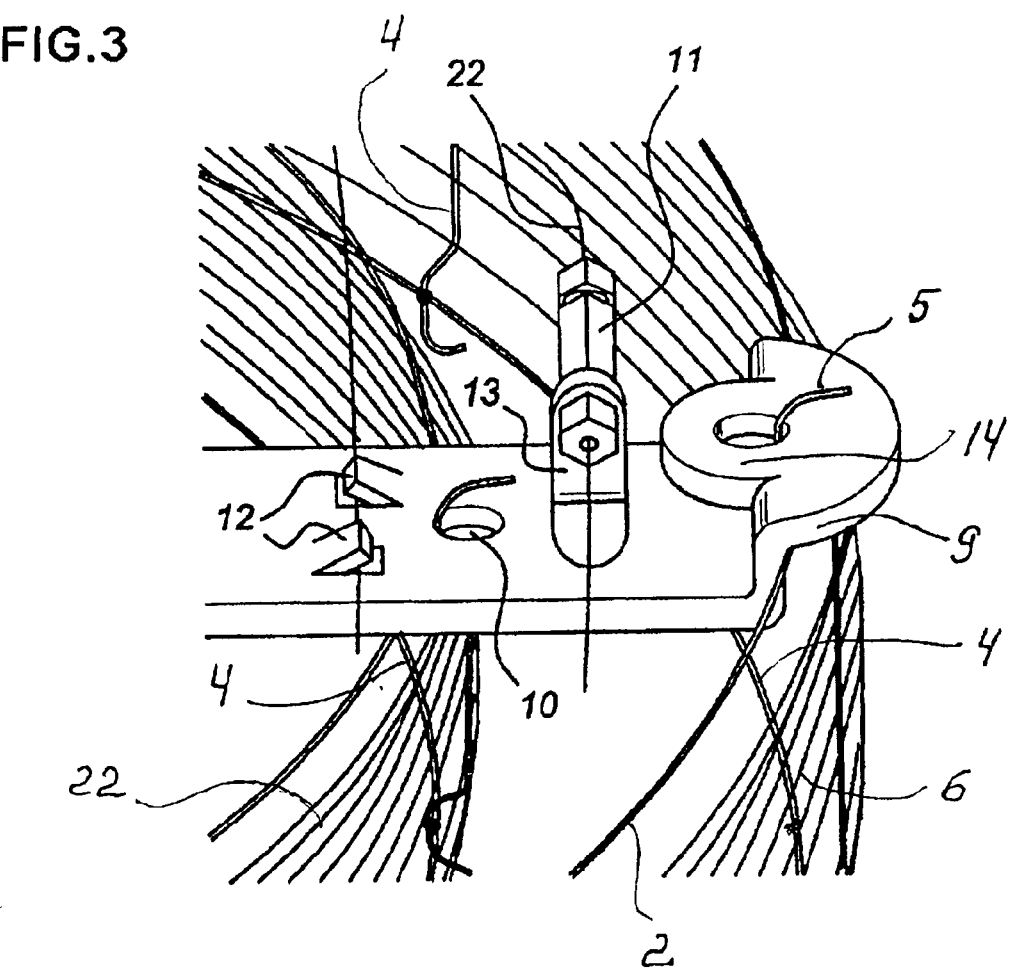
FIG. 3 shows an enlarged view of part of FIG. 2.

In addition to apertures 8, proximate opposite ends of the elongate carrier 7, a further pair of apertures 10 can be provided to accommodate a second winding structure 21, on which a different column 22 is wound, as shown in FIGS. 2 and 3. The further apertures 10 are spaced inwardly of the apertures 8. The winding structure 21 has a smaller diameter than the winding structure 1 and is positioned concentrically within the winding structure 1. The winding structure 21 has a similar general configuration to the winding structure 1, and is attached to the carrier 7 in a similar manner—by the passage of a semicircular or hook-like portion passing through respective apertures 10.

A member 13 extends from the carrier 7 for accommodating a connector 11 for coupling together the two columns 6 and 22. Clips 12 are provided on the carrier 7 for accommodating the beginning and end of one or more of the columns 6, 22. These clips may be formed by making a U-shaped cut in the surface of the carrier 7 to form a tab, which is bent away from the surface so that the tab is inclined with respect to the main surface of the carrier 7. Four clips 12 are provided in total, with pairs of clips being located side by side and extending in opposite directions to restrict lateral movement of the column 6 or 22.

The carrier 7 is writable with information, for example, information regarding the or each column to which it is attached. Further, the carrier 7 provides a convenient means by which the column or columns may be carried. The carrier 7 acts as a grip, handle or toolbar. Furthermore, the column ends can be located or "parked" using the clips 12 of the carrier 7.

Figure 4:
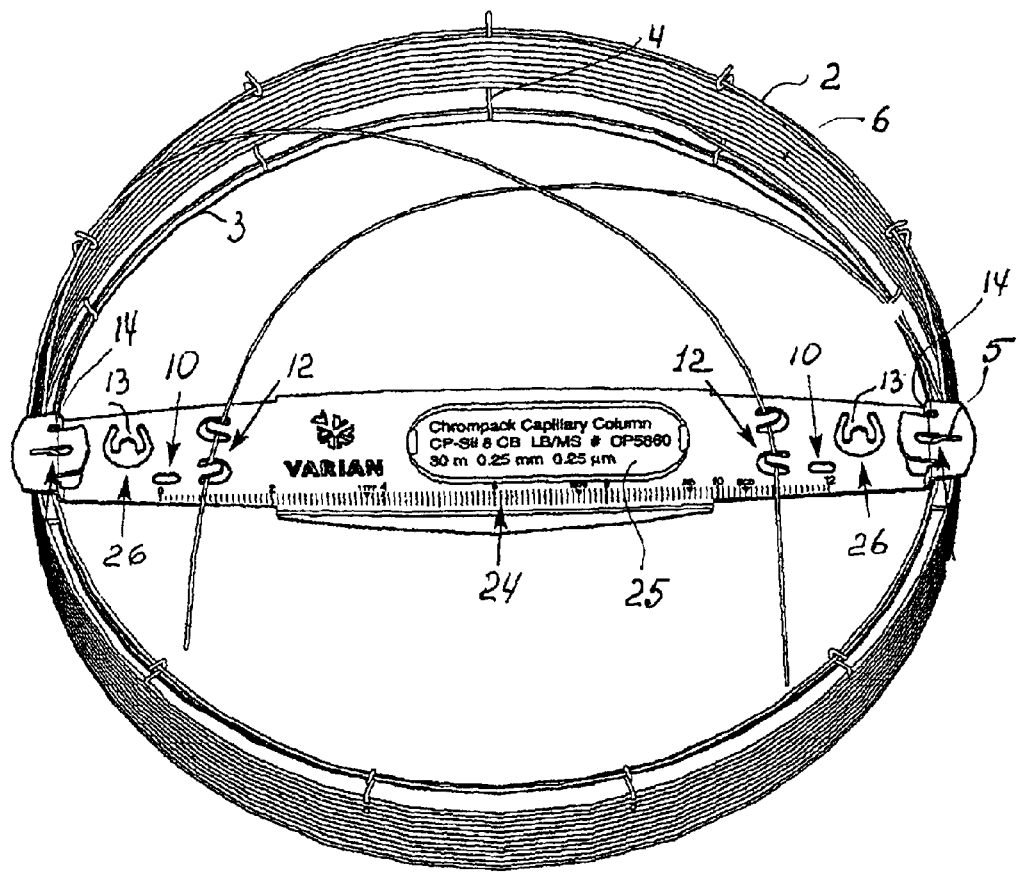
FIG. 4 shows a perspective view of a chromatographic column and information carrier without a connector attached.
Figure 5:
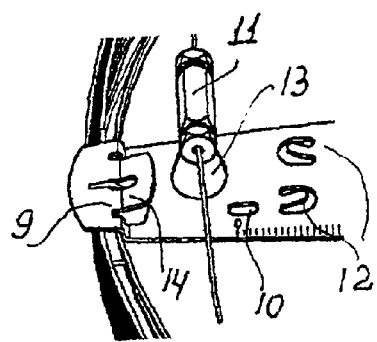
FIG. 5 shows a partial view of the information carrier of FIG. 4 with a connector attached thereto.

FIGS. 4 and 5 show a modified form of carrier 7. In FIG. 4, the carrier 7 includes a ruler scale 24, marked in inches or centimeters. A label 25 is provided on which information about the column 6 is displayed. FIG. 4 also shows mounting locations 26 for mounting the connector 11. The member 13 is bent perpendicularly from the plane of the carrier 7 when it is required to form a mounting bracket for the connector 11. FIG. 5 shows the connector 11 in place.

Although preferred embodiments of the invention have been described, it will be clear to those skilled in the art that numerous adaptations can be added that departing from the spirit or scope of the present invention. For example, it is possible to redesign the carrier 7 at its ends to alter the connection with the winding structure 1, 21. Also, further tools and features which are used with chromatographic columns, can be added or attached to the carrier 7.

What is claimed is:

1. A chromatographic column assembly comprising:
   a column support structure comprising at least one ring,
   a wound tubular chromatographic column mounted on the column support structure, and
   a carrier connected to the support structure along the at least one ring, extending generally along a plane of the at least one ring between opposite sides of the at least one ring, the carrier including at least one connecting part for connecting the carrier to the support structure.

2. An assembly according to claim 1, wherein the carrier is in the form of a strip.

3. An assembly according to claim 1, wherein the at least one connecting part comprises an aperture in the carrier.

4. An assembly according to claim 1, the carrier including a further connecting part for connecting the carrier to a further chromatographic column assembly comprising a further support structure and a further wound chromatographic column mounted on the further support structure.

5. An assembly according to claim 1, wherein the carrier comprises metal.

6. An assembly according to claim 1, wherein the carrier includes at least one part adapted for mounting a chromatographic column connector thereon.

7. An assembly according to claim 1, wherein the carrier includes at least one part for displaying information.

8. An assembly according to claim 1, the carrier including a device for holding a chromatographic column.

9. An assembly according to claim 1, the carrier including a measurement indicia.

10. An assembly according to claim 1, wherein the column support structure includes one or more connectors for connecting to the carrier.

11. An assembly according to claim 10, wherein each connector comprises a hook.

12. An assembly according to claim 10, wherein the column support structure comprises upper and lower rings connected by a plurality of connecting bars, at least one of the connecting bars forming the one or more connectors.

13. A chromatography column assembly comprising:
   a first column support structure comprising a pair of generally parallel rings connected by a plurality of connecting bars, each of the connecting bars extending between a first ring of the pair of rings and a second ring of the pair of rings,
   a first tubular gas chromatographic column wound around the first column support structure; and
   a strip-shaped carrier attached to the first column support structure substantially at two opposite ends of the carrier, for allowing a user to carry the chromatographic column assembly, the carrier being connected to the column support structure along at least one of the pair of rings, and extending generally along a plane of the at least one of the pair of ring between opposite sides of the at least one of the pair of rings.

14. The assembly of claim 13, further comprising a second column support structure and a second tubular gas chromatographic column wound around the second column support structure, wherein the second column support structure is positioned concentrically within the first column support structure and is attached to the carrier.

15. A method of assembling a gas chromatographic column assembly, comprising:
   winding a first tubular gas chromatographic column around a first column support structure, the first column support structure comprising at least one ring;
   connecting a carrier to the support structure along the at least one ring, such that the carrier extends generally along a plane of the at least one ring between opposite sides of the at least one ring, the carrier including at least one connecting part for connecting the carrier to the support structure.

16. The method of claim 15, further comprising:

winding a second tubular gas chromatographic column around a second column support structure;

disposing the second column support structure concentrically within the first column support structure; and attaching the carrier to the second column support structure.

17. A chromatographic column assembly comprising:

a chromatographic column support structure for winding a chromatographic column thereon, the column support structure comprising at least one ring, and a carrier connected to the support structure at opposite sides of the at least one ring, and extending generally along a plane of the at least one ring.

18. An assembly according to claim 17, wherein the carrier is shaped as a strip having a major surface substantially parallel to the plane of the at least one ring.

19. An assembly according to claim 17, wherein the column support structure comprises a pair of hooks situated along opposite sides of the at least one ring, and wherein the carrier comprises a first pair of apertures positioned at opposite ends of the carrier, for receiving the pair of hooks to secure the carrier to the column support structure.

20. An assembly according to claim 17, wherein the carrier comprises a second pair of apertures positioned inward relative to the first pair of apertures, for receiving a further pair of hooks of a further column support structure.

21. An assembly according to claim 17, further comprising a chromatographic column connector mounted on the carrier, for fluidically connecting to the chromatographic column.

22. An assembly according to claim 17, wherein the carrier includes an information display substantially parallel to the at least one ring.

23. An assembly according to claim 22, wherein the information display comprises a distance measurement indicator.

24. An assembly according to claim 17, wherein the column support structure comprises upper and lower parallel rings connected by a plurality of connecting bars, the connecting bars supporting the chromatographic column.

* * * * *